United States Patent
Otero et al.

(10) Patent No.: US 6,475,768 B1
(45) Date of Patent: Nov. 5, 2002

(54) XYLOSE ISOMERASE WITH IMPROVED PROPERTIES

(75) Inventors: Ricardo Román Cordero Otero, Stellenbosch (ZA); Márk Gárdonyi; Bärbel Hahn-Hägerdal, both of Lund (SE); Willem Heber van Zyl, Stellenbosch (ZA); Eva Anna Viktoria Dackehag, Lund (SE)

(73) Assignee: Forskarpatent I Syd AB, Lund (SE)

( * ) Notice: Subject to any disclaimer, the term of this patent is extended or adjusted under 35 U.S.C. 154(b) by 0 days.

(21) Appl. No.: 09/545,569

(22) Filed: Apr. 7, 2000

(51) Int. Cl.$^7$ ............................. C12N 9/90; C12N 15/61
(52) U.S. Cl. ............... 435/233; 435/254.2; 435/254.21; 435/254.22; 435/254.23; 435/320.1; 435/161; 536/23.2
(58) Field of Search ............................. 435/233, 320.1, 435/254.2, 161, 254.21, 254.22, 254.23; 536/23.2

(56) References Cited

U.S. PATENT DOCUMENTS

| | | | |
|---|---|---|---|
| 4,894,331 A | | 1/1990 | Ratzkin et al. ............... 435/94 |
| 5,411,886 A | * | 5/1995 | Udaka et al. ............ 435/252.3 |

FOREIGN PATENT DOCUMENTS

| | | |
|---|---|---|
| EP | 0 483 691 A2 | 5/1992 |
| WO | WO 90/00196 | 1/1990 |
| WO | WO 96/24667 | 8/1996 |

OTHER PUBLICATIONS

Amore et al., "The Fermentation of Xylose—An Analysis of the Expression of Bacillus and Actinoplanes Xylose Isomerase Genes in Yeast", *Applied Microbiology and Biotechnology*, 30:351–457, 280698 (1989).
Bradford, "A Rapid and Sensitive Method for the Quantitation of Microgram Quantities of Protein Utilizing the Principle of Protein–Dye Binding", *Analytical Biochemistry*, 72:248–254, 290176 (1976).
Dekker et al., "Efficient Production of Thermostable Thermus Thermophilus Xylose Isomerase in Escherichia Coli and Bacillus Brevis", *Applied Microbiology Biotechnology*, 36:727–732, 311091 (1992).
Gietz et al., "New Yeast Escherichia Coli Shuttle Vectors Constructed With In Vitro Mutagenized Yeast Genes Lacking Six–Base Pair Restriction Sites", (Elsevier Science Publishers), 300988 (1988).
Reichelt, "Starch", Industrial Enzymology: Practical Approaches, *The Nature Press*. pp. 375–388 (1983).
Kuhn et al, "Purification and Partial Characterization of an Aldo–Keto Reductase from Saccharomyces Cerevisiae", *Applied and Environmental Microbiology*, vol. 61, No. 4, pp. 1580–1585, 060295 (1995).

Mellor et al. "Efficient Synthesis of Enzymatically Active Calf Chymosin in Saccharomyces Cerevisiae", *Gene*, vol. 24, pp. 1–14, 230483 (1983).
Moes et al., "Cloning and Expression of the Clostridium Thermosulfurogenes D–Xylose Isomerase Gene (xyIA) in Saccharomyces Cerevisiae", *Biotechnology Letters*, vol. 18, No. 3, pp. 269–274 (1996).
Richard et al., "Evidence that the Gene YL070c of Saccharomyces Cerevisiae Encodes a Xylitol Dehydrogenase", *FEBS Letters*, 457:135–138, 190799 (1999).
Sarthy et al., "Expression of the Escherichia Coli Xylose Isomerase Gene in Saccharomyces Cerovisiae", *Applied and Environmental Microbiology*, vol. 53, No. 9, pp. 1996–2000, 020687 (1987).
Tantirungkij et al., "Construction of Xylose–Assimilating Saccharomyces Cerevisiae", *Journal of Fermentation and Bioengineering*, vol. 75, No. 2, pp. 83–88, 201192 (1993).
Walfridsson et al., "Ethanolic Fermentation of Xylose with Saccharomyces Cerevisiae Harboring the Thermus Thermophilus xyIA Gene, Which Expresses an Active Xylose (Glucose) Isomerase", *Applied and Environmental Microbiology*, vol. 62, No. 12, pp. 4648–4651, 220996, (1996).
Yamanaka, "Inhibition of D–Xylose Isomerase by Pentitols and D–Lyxose", *Archives of Biochemistry and Biophysics*, 131:502–506, 180269 (1969).
Gietz et al., "High Efficiency Transformation with Lithium Acetate", *Molecular Genetics of Yeast, Practical Approaches*, Oxford University Press, pp. 121–134 (1994).

* cited by examiner

Primary Examiner—Charles L. Patterson, Jr.
(74) Attorney, Agent, or Firm—Finnegan, Henderson, Farabow, Garrett & Dunner, LLP

(57) ABSTRACT

The present invention relates to novel nucleic acid sequences which, upon expression in a procaryotic or eucaryotic cell, code for a polypeptide having an elevated specific xylose isomerase activity compared to the wildtype *Thermus thermophilus* xylose isomerase. They are selected from a) nucleic acid sequences shown in SEQ. ID. No 1; b) the complementary strand of the sequence defined in (a) above; c) nucleic acid sequences which hybridize to the sequences defined in (a) or (b) above; d) nucleic acid sequences which, but for the degeneracy of the genetic code, would hybridize to the sequences defined in (a), (b) or (c) above and which code for the same polypeptide as those defined in (a), (b) or (c) above. The present invention further provides a process of producing ethanol from xylose containing materials comprising contacting cells that express such nucleic acid sequences and novel modified xylose isomerases that advantageously can be applied in the production of fructose syrups.

29 Claims, 5 Drawing Sheets

XYLOSE ISOMERASE WITH IMPROVED PROPERTIES

TECHNICAL FIELD

Figure 1:
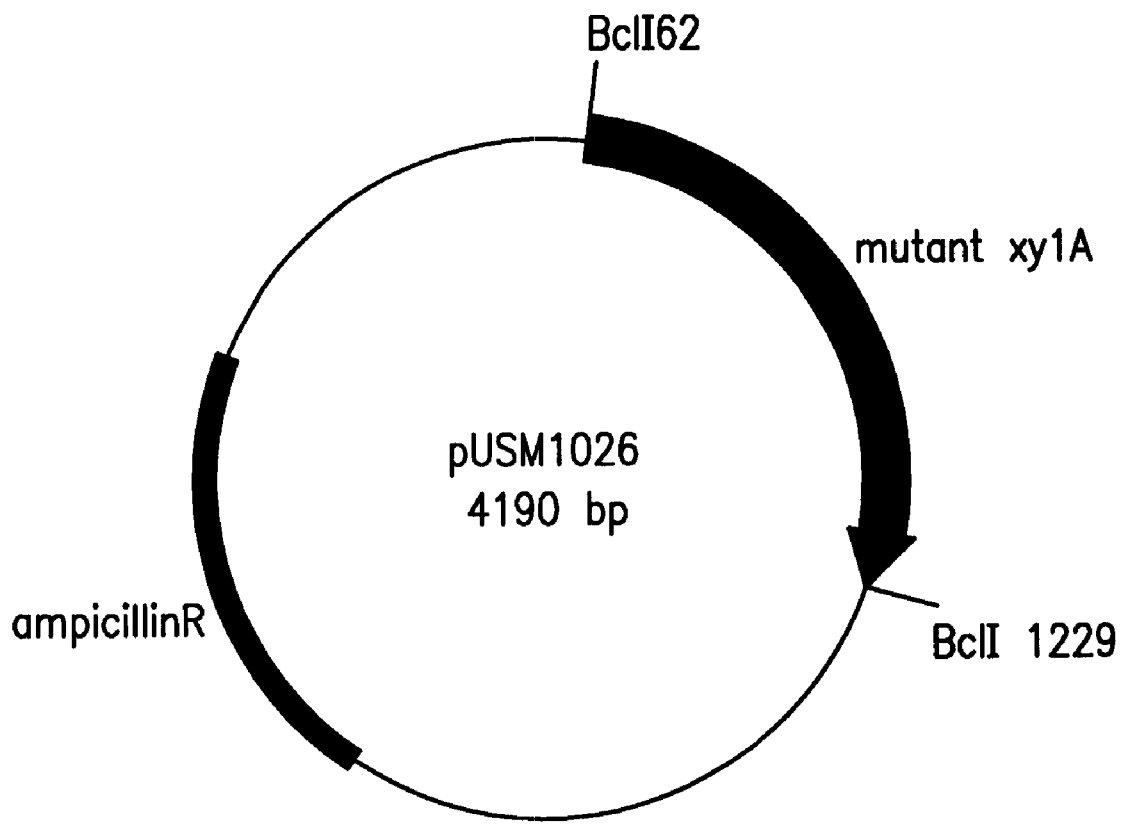

This invention relates to nucleic acid sequences encoding novel modified xylose isomerases, to vectors carrying the sequences, to the polypeptides encoded by these sequences, to the production of a polypeptide encoded by these sequences and to the use of the isomerase in a process of ethanol production. The present invention further provides novel modified xylose isomerases that advantageously can be applied in the production of fructose syrups, in particular high fructose corn syrups.

BACKGROUND ART

D-xylose is a five-carbon sugar. It is present in nature, for example as xylan polymer in plant hemicellulose. As a carbon source, D-xylose has been reported to be utilised widely by bacteria and to a lesser extent by fungi. D-xylose is first converted to its keto isomer, D-xylulose, which is then phosphorylated to D-xylulose-5-phosphate, a normal pentose phosphate pathway intermediate.

There are two possible routes for the isomerisation of D-xylose: (a) direct conversion to D-xylulose by an isomerase; or (b) an oxidoreductive pathway, in which D-xylose is first reduced to xylitol and in a second reaction xylitol is oxidised to D-xylulose. The enzymes involved in this oxidoreductive pathway require coenzymes. The direct isomerisation is reported from bacteria and plant, while the oxidoreductive pathway is the main route for D-xylose to D-xylulose conversion in fungi.

Xylose isomerase catalyses the direct isomerisation of D-xylose to D-xylulose and vice versa, with the direction dependent on the relative concentration of the aldo and keto forms and the reaction conditions. Xylose isomerase also catalyses of interconversion of the 6carbon aldose sugar D-glucose and its keto isomer D-fructose. Thus, bacterial xylose isomerases are used industrially to produce D-fructose from D-glucose.

The economic use of lignocellulosic biomass as a renewable energy source is strongly dependent on the fermentation of xylose to ethanol. Since the best ethanol-producing organism, *Saccharomyces cerevisiae* is not able to utilise xylose, major efforts have been taken to develop recombinant strains possessing the necessary enzymes. The xylose reductase and xylitol dehydrogenase from *Pichia stipitis* were cloned and expressed in *Saccharomyces cerevisiae*. The resulting strains were able to ferment xylose, however the yields were far from the theoretical due to the xylitol excretion (Tantirungkij et al. (1993)).

Several attempts to circumvent this problem by introducing the alternative direct isomerisation pathway have been made. The xylose isomerases form two clusters based on the sequence homology, the actinomycetic genes showing less than 40% homology to the others. From the latter subgroup the *Bacillus subtilis* (Amore et al. (1989)) and the *Escherichia coli* (Sarthy et al. (1987)) xylose isomerases were expressed inactively in *Saccharomyces cerevisiae*, while introduction of the *Clostridium thermosulfurogenes* (Moes et al. (1996)) gene did not result in a protein that cross-reacted with a specific antibody. From the first subgroup the *Actinoplanes missouriensis* (Amore et al. (1989)) gene was cloned in yeast but the production of xylose isomerase failed due to an aberrant transcription start.

The *Thermus thermophilus* xylose isomerase only recently has been actively expressed in *Saccharomyces cerevisiae* (Walfridsson et al. (1996)). This gene is closely related to the actinomycetic genes showing approximately 65% homology. The enzyme, however, has only trace activity at 30° C., because of its high (95° C.) temperature optimum. The other important factor for the poor performance of the strain was the formation of xylitol, probably by the unspecific NADPH linked aldose reductase described by (Kuhn et al. (1995)), which is coded by the gene GRE3. The xylitol formation has a dual effect on the ethanol yield; it does not only lead to carbon loss, but it also competitively inhibits the xylose isomerase (Yamanaka (1969)). By increasing intracellular xylitol concentration the apparent affinity of the xylose isomerase towards xylose decreases and more xylose is channelled into xylitol, until the NADPH pool of the cell is depleted. In the presence of active xylose isomerase some xylitol can be formed also by the endogenous xylitol dehydrogenase described by (Richard et al. (1999)). To prevent the xylitol impairing the xylose isomerase and thereby blocking the xylose metabolism of the recombinant yeast, it is advantegous to have a xylose isomerase expressed which is less sensitive to the presence of xylitol.

DISCLOSURE OF THE INVENTION

In light of the previously described problems, there is a need to find a xylose isomerase being actively expressed in *Saccharomyces cerevisiae* and being more active at a broader range of pH values and temperatures.

In the present invention, a series of novel xylose isomerases have been isolated. They were modified from the *Thermus thermophilus* enzyme by random mutagenesis and identified as having elevated activity at mesophilic (<40° C.) temperatures, compared to the wild type enzyme. Expressed either in procaryotic or eucaryotic cells, the specific enzyme activity in the mutants is at least 10% higher than that of the wildtype enzyme. They are, therefore, expected to be more suitable for expression in yeast. The present invention thus comprises any isolated nucleic acid sequence which upon expression in a procaryotic or eucaryotic host cell codes for a polypeptide having at least 10% higher specific xylose isomerase activity, than the wild type xylose isomerase which nucleic acid sequence is shown in SEQ. ID. No. 2. The specific activity of the enzyme is to be determined as described in example 3, wherein one unit of xylose (glucose) isomerase activity is defined as the amount of crude enzyme needed to produce 1 μmol of product per minute under the assay conditions. The specific activity (U $min^{-1}$ $mg^{-1}$) is herein determined from the activity and the protein concentration of the crude enzyme preparations.

The present invention further comprises any isolated nucleic acid sequence that is derived and shows at least one nucleic acid modification from the nucleic acid sequence shown in SEQ. ID. No. 2.

Furthermore, the mutants show a higher thermostability than the wildtype enzyme. One embodiment of the invention thus comprises an isolated nucleic acid sequence which upon expression in a procaryotic or eucaryotic host cell codes for a polypeptide having at least 10% higher specific xylose isomerase activity at temperatures above 80° C. such as 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C. and/or 100° C., than the wild type xylose isomerase which nucleic acid sequence is shown in SEQ. ID. No. 2.

In another embodiment of the invention, the mutants also show a higher acceptance for xylitol, which is an inhibitor to xylose isomerase, compared to the wildtype enzyme.

In a further embodiment of the invention, the mutated xylose isomerases have a broader pH range than the wildtype, even though it may have the same pH optimum at ~7.0. The present invention therefor also comprises any isolated nucleic acid sequence which upon expression in a procaryotic or eucaryotic host cell codes for a polypeptide having at least 10% higher specific xylose isomerase activity at acidic pH values i.e. lower than pH 7.5 such as pH 7.4, pH 7.3, pH 7.2, pH 7.1, pH 7.0, pH 6.9, pH 6.8, pH 6.7, pH 6.6, pH 6.5, pH 6.4, pH 6.3, pH 6.2, pH 6.1, pH 6.0, pH 5.9, pH 5.8, pH 5.7, pH 5.6, pH 5.5, pH 5.4, pH 5.3, pH 5.2, pH 5.1, pH 5.0, pH 4.5 and/or pH 4.0 than the wild type xylose isomerase which nucleic acid sequence is shown in SEQ. ID. No. 2.

In a preferred embodiment, the present invention provides:

An isolated nucleic acid sequence which codes upon expression in a procaryotic or eucaryotic host cell for a polypeptide having xylose isomerase activity at mesophilic temperatures, which nucleic acid sequence is selected from a) nucleic acid sequences shown in SEQ. ID. No 1, wherein nnn at positions 1114–1116 stand for a codon coding for an amino acid other than glutamate, preferably a codon coding for glycine and nnn at positions 487–489 stand for a codon coding for any amino acids, preferably phenylalanine, more preferably leucine b) the complementary strand of the sequence defined in (a) above;

c) nucleic add sequences which hybridise to the sequences defined in (a) or (b) above and the residues corresponding to the residues nnn and nnn in SEQ. ID. No 1 are as defined in (a) or (b) above;

d) nucleic acid sequences which, but for the degeneracy of the genetic code, would hybridise to the sequences defined in (a), (b) or (c) above and which code for the same polypeptide as those defined in (a), (b) or (c) above;

a polypeptide encoded by a nucleic acid sequence as defined above;

a vector comprising a nucleic acid sequence as defined above;

cells transformed or transfected with such a vector; a process of producing ethanol which comprises:

(i) contacting such transformed cells with a substrate that contains one or more carbon sources selected from xylose and polymerised xylose moieties;

(ii) culturing the said cells in conditions under which the isomerisation of D-xylose to D-xylulose occurs and under which the D-xylulose is further catabolised to ethanol; and (iii) recovering the ethanol;

a process of producing a polypeptide as defined above comprising expressing a nucleic acid sequence as defined above in a cell as defined above;

a process of producing D-fructose which comprises:

(i) contacting such polypeptide with a substrate containing D-glucose;

(ii) incubating the substrate with the polypeptide in conditions under which the isomerisation of D-glucose to D-fructose occurs;

(iii) recovering the mixture of D-glucose and D-fructose

The nucleic acid sequences of the present invention are preferably DNA, though they may be RNA or even PNA. It will be obvious to those of skill in the art that, in RNA sequences according to the invention, the T residues shown in SEQ. ID. No. 1 will be replaced by U.

The nucleic acid sequences of the present invention include in the sequence shown in SEQ. ID. No. 1, wherein the nnn at the positions 1114–1116 stand for a nucleotide triplet, which upon expression codes for an amino acid other than glutamate, preferably glycine. Such nucleotide triplet is for example GGA. Similarly, the nnn at the positions 487–489 stand for a nucleotide triplet, which upon expression codes for any amino acid, preferably phenilalanine, more preferably leucine. Such a nucleotide triplet is for example CTC.

As apparent from the ove, the nucleic acid sequences of the present invention are not limited to the sequences of SEQ. ID. No 1. Rather, the sequences of the invention include sequences that are closely related to these sequences and that encode a polypeptide having xylose isomerase activity, xylose isomerase activity being the ability to catalyze the direct interconversion of xylose to xylulose. For example, four preferred sequences of such polynucleotides are shown in SEQ. ID. No. 3, 5, 7, and 9. These nucleic acid sequences may be prepared by altering SEQ. ID. No. 1 by any conventional method, or they may be isolated from an organism or made synthetically. Such alterations, isolations, or syntheses may be performed by any suitable method, for example by the methods of Sambrook et al. (Sambrook et al. (1989)).

For example, the sequences of the invention include sequences that are capable of selective hybridisation to those of SEQ. ID. No. 1; preferably those wherein the residues selectively hybridising to the residues marked as nnn in SEQ. ID. No. 1 are coding for an amino acid other than glutamate, preferably glycine; and which code for a polypeptide having xylose isomerase activity. Such hybridisation may be carried out under any suitable conditions known in the art (see Sambrook et al. (1989)). "Hybridisation" is a process in which a strand of nucleic acids joins with a complementary strand through base pairing. The degree of complementarity of two non-identical, but very similar strands, and their length influence the hybridisation conditions. In the present invention, the conditions for hybridisation are meant to be those of a stringent hybrisisation according to (Sambrook et al. (1989)).

Also the sequences of the invention include sequences that are different from those defined above because of the degeneracy of the genetic code and encode the same polypeptide. Degenerate code stands for a genetic code in which a particular amino acid can be coded by two or more different codons. Degeneracy occurs because of the fact that of the 64 possible base triplets, 3 are used to code the stop signals, and the other 61 are left to code for only 20 different amino acids.

Terms and abbreviations in this document have their normal meanings unless otherwise stated. All nucleic acid sequences are written in the direction from the 5'(stands for prime) end to the 3' end also referred to as 5' to 3'. All amino acid or protein sequences, unless otherwise designated, are written from the amino terminus (N-terminus) to the carboxy terminus (C-terminus).

The codon usage is the standard published and internationally used single or triple letter amino acid code.

The word "base pair" or "bp" refers to DNA or RNA. The single letters A, C, T and G correspond to the 5-monophosphate forms of the deoxyribonucleosides (deoxy)adenine, (deoxy)cytidine, (deoxy)guanine and (deoxy)thymidine, respectively. Furthermore, the abbreviations U, C, G and T may correspond to the 5'-monophosphate forms of the ribonucleosides uracil, cytidine, guanine and thymine, respectively, occurring in RNA molecules. "Base pair" in double stranded DNA refers to a pairing of A with T or C with G. In a heteroduplex of RNA paired with DNA, base pair may refer to a pairing of A with U or C with G.

The term "vectorz" stands for a nucleic acid compound used for the transformation of cells. A vector contains a polynucleotide sequence corresponding to appropriate protein molecules which, when combined with appropriate control sequences, confer specific properties on the host cell to be transformed. Plasmids, viruses and bacteriophage are suitable vectors. Artificial vectors can be constructed by cutting and joining DNA molecules from different sources using restriction enzymes and ligases. The term vector also includes recombinant DNA cloning vectors and recombinant DNA expression vectors.

The term "Promoter" stands for a DNA sequence which directs transcription of DNA to RNA, The term "plasmid" refers to an extrachromosomal (usually) self-replicating genetic element. Plasmids are commonly designated by a lower case "p" followed by letters or numbers. The plasmids used here are either commercially available, publicly available on an unrestricted basis or can be constructed from available plasmids following published procedures. In addition, equivalent plasmids to those described are known and are apparent to the skilled worker in this field.

"Transformation" means the introduction of DNA into an organism in a way that it can replicate itself, either as an extrachromosomal element or by chromosomal integration. Methods of transforming bacterial and eukaryotic hosts are well known. Many of these methods, such as nuclear injection, protoplast fusion or calcium treatment with calcium chloride are summarized in (Sambrook, et al. (1989)).

"Transfection" is the operation of adding an expression vector to a host cell, whereby the cell itself takes up the DNA molecule and either integrates it into the chromosomes (stable transfection) or keeps it separate from the chromosomal DNA in the nucleus as a transient transcribed plasmid (transient transfection). Many different methods of transfection are known, for example calcium phosphate co-precipitation and electroporation. A successful transfection can be monitored by a specific site introduced in the transfected DNA molecule which can be recognised by an antibody. This DNA site can either be a specifically introduced "flag" or "tag" meaning a specific sequence which is easily recognised by an antibody. It could also be an intrinsic part of the expressed gene, recognised by a specific antibody. Another possibility would be the fusion to a fluorescent protein like eg GFP (green fluorescent protein).

The expressions "complementary" and "complementarity" refer to the matter of base pairing of purines and pyrimidines that associate through hydrogen bonding in double stranded nucleic acid. The base pairs guanine and cytosine, adenine and thymidine as well as adenine and uracil are complementary.

"Isolated amino acid sequence" refers to any amino acid sequence, constructed or synthesised, which is locationally distinct from the naturally occurring sequence.

A "primer" is a nucleic acid fragment, which functions as an initiating substrate for enzymatic or synthetic elongation.

The term "a polypeptide" in the present application is generally understood to mean a polypeptide of the invention, as shown for example in SEQ. ID. No. 4, 6, 8, or 10. It is also within the meaning of "a polypeptide" that several polypeptides can be used, i.e. in the present context "a" means "at least one" unless explicitly indicated otherwise.

The sequence "identity" can be calculated as $$\frac{(N_{ref} - N_{dif})100}{N_{ref}},$$

wherein $N_{dif}$ is the total number of non-identical residues in the two sequences when aligned, and wherein $N_{ref}$ is the number of residues in one of the sequences. Hence, the DNA sequence AGTCAGTC will have a sequence identity of 75% with the sequence AATCMTC ($N_{dif}=2$ and $N_{ref}=8$). A gap is counted as non-identity of the specific residue(s), ie the DNA sequence AGTGTC will have a sequence identity of 75% with the DNA sequence AGTCAGTC ($N_{dif}=2$ and $N_{ref}=8$). Sequence identity can alternatively be calculated by the BLAST program, eg the BLASTP program (Pearson W. R and D. J. Lipman (1988))(www.ncbi.nlm.nih.gov/cgi-bin/BLAST). Alignment can be performed with the global align algorithm with default parameters as described by (Huang and Miller (1991)), available at http://www.ch.embnet.org/software/LALIGN_form.html.

One preferred embodiment of the invention thus comprises a nucleic acid sequence, which nucleic acid sequence is identical at least 85%, such as at least 90%, at least 95%, at least 99% or at least 100% to any of the sequences defined above.

A yeast expressing active xylose isomerase can be used in a process for producing ethanol from xylose containing materials. Suitable substrates for ethanol production include xylose itself and any compound that the cells can convert into xylose. For example, suitable substrates include polymers that contain xylose moieties. Thus, xylan, arabinoxylan and xyloglucan polymers, which comprise xylose moieties, are suitable substrates. Accordingly, hemicellulosic and lignocellulosic substrates, such as plant biomass, are suitable substrates.

In processes of ethanol production according to the present invention, xylose is typically released from xylan by enzymatic or chemical hydrolysis under acidic or basic conditions, or by heating or by a combination of these techniques. For example xylose can be released from xylan by a combination of acidic hydrolysis and heating under pressure. The yeasts typically used in ethanol production are not capable of enzymatically hydrolysing xylans to release xylose, although some yeasts are capable of doing so and of metabolising the xylose to ethanol. Such yeasts, when transformed with a vector according to the invention, are included within the scope of the invention.

Although the preferred processes of ethanol production according to the invention comprise contacting transformed or transfected cells with a suitable substrate, other processes of producing ethanol are also possible. For example, a polypeptide according to the invention may be added to a cellular fermentation broth in order to liberate xylose outside the cells, which is then taken up and metabolised by them.

In the present invention, ethanol will typically be produced by a fermentation broth that comprises yeast cells according to the invention, water, one or more sources of xylose and other nutrients. These nutrients preferably include a suitable nitrogen source, such as (NH4)2SO4. The presence of hexose sugars, such as glucose may enhance both ethanol formation productivity and growth. Also, the presence of Mn2 or Mg2 ions is desirable as one of these ions is necessary to the function of the mutant xylose isomerases. Further, the presence of low levels of oxygen is desirable, especially in fermentation broths containing Saccharomyces cerevisiae.

The process may be carried out at any temperature that facilities ethanol production, but temperatures from 15 to 40° C. are preferred and temperatures from 30 to 35° C. are particularly preferred. In one embodiment of the present invention, the novel xylose isomerases therefor show at least 10% elevated activity at temperatures ranging from 20–60° C., such as in an especially preferred embodiment at 30–35° C.

For the ethanol-producing processes of the invention, it is preferred that transformed or transfected yeast cells, especially those of S. cerevisiae are used. Recently a *Saccharomyces cerevisiae* strain was constructed with the GRE3 gene disrupted (WO99/54477). This strain shows reduced levels of xylitol formation, when it is metabolising xylose. In one preferred embodiment of the invention, cells of a *S. cerevisiae* strain according to the patent application (WO99/54477) are used. As the person skilled in the art will be aware of, though, this should not exclude the possible usage of other transfected yeast cells, such as a cell of a species selected from a list that should be regarded only as illustrative and not exclusive, consisting of Pichia sp., Candida sp., Shizosaccharomyces sp., Zygosaccharomyces sp. and Saccharomyces sp. Furthermore, other Saccharomyces families are embodied in the scope of the invention, for example; *Saccharomyces cerevisisae, Saccharomyces bayanus* and *Saccharomyces carlsbergensis*.

In the ethanol-producing processes of the invention, the substrate is wholly or partly converted to ethanol, which may be recovered by any suitable means known in the art. The xylose isomerases according to the invention are also suitable for industrial high fructose syrup production. In this process D-glucose, preferably in the form of starch hydrolysate, is partially converted to D-fructose. Typical process conditions are 60° C., pH 7.5 with 45 ppm Mg2+ and 45% w/w D-glucose as substrate. The substrate is preferably obtained as starch hydrolysate, produced for example from wheat starch with the methods described in (Godfrey and Reichelt (1983)).

In a conventional industrial process, the aim is, in most cases, to obtain a sugar solution, in which 40 to 45% of the sugar is fructose. When the activity of the enzyme decreases with the ageing of the column, the desired level is maintained by reducing the flow rate.

EXAMPLES

Example 1
Random Mutagenesis of the xylA Gene

The xylA gene of the *Thermus thermophilus* was amplified using polymerase chain reaction (PCR) from the pBXI plasmid (Walfridsson et at (1996)) as template. Three samples with the following (identical) composition were prepared:

|  | Volume (μl) |
|---|---|
| Template (0.1 μg/μl) | 0.5 |
| Buffer10X | 5.0 |
| dNTP mix (10 mM each) | 1.0 |
| Primer 1:xylA R | 5.0 |
| Primer 2:xylA L | 5.0 |
| MgCl$_2$ | 5.0 |
| H$_2$O | 28.0 |
| Taq polymerase 5 u/μl | 0.5 |
| Total Volume | 50.0 |

The nucleic acid sequence of Primer 1 is shown in SEQ. ID. No.11, that of Primer 2 is shown in SEQ. ID. No. 12.

The samples were placed in a thermocycler (Perkin Elmer GeneAmp2400) and subjected to the following temperature program, where the 2$^{nd}$ segment was repeated 6 times:

Temperature program:

| Segment | Step | Temperature | Time | Performed |
|---|---|---|---|---|
| 1. | denaturation | 94° C. | 2 min | once |
| 2. | denaturation | 94° C. | 30 sec | numbers |
|  | annealing | 69.5° C. | 30 sec | indicated in the |
|  | extension | 72° C. | 45 sec | text |
| 3. | extension | 72° C. | 8 min | once |

The samples were mixed and divided again into three aliquots to equalise the concentrations. The following reagents were added to these samples:

| Sample: | A (50 μl) | B (50 μl) | C (50 μl) |
|---|---|---|---|
|  | Volume added (μl) | | |
| MgCl$_2$ (25 mM) | 5.0 | 5.0 | 5.0 |
| dNTP mix (10 mM each) | 1.0 | — | — |
| Unbalanced dNTP mix* | — | 10.0 | 10.0 |
| Buffer10X | 5.0 | 5.0 | 5.0 |
| MnCl$_2$ (10 mM) | — | 1.5 | — |
| H$_2$O | 38.5 | 28.0 | 29.5 |
| Taq polymerase (5 U/μl) | 0.5 | 0.5 | 0.5 |
| Total volume: | 100 | 100 | 100 |

*The unbalanced dNTP mix contained 2 mM dATP and dGTP and 10 mM dCTP and dTTP, each.

The temperature program described above was performed in the thermocycler mentioned above with a single 2.segment. Half of the samples (50 μl) was removed and saved on −20° C. (samples A1, B1 and C1). To the remaining 50 μl samples the following reagents were added:

| Sample: | A1 (50 μl) | B1 (50 μl) | C1 (50 μl) |
|---|---|---|---|
|  | Volume added (μl) | | |
| MgCl$_2$ (25 mM) | 5.0 | 5.0 | 5.0 |
| dNTP mix (10 mM each) | 1.0 | — | — |
| Unbalanced dNTP mix | — | 5.0 | 5.0 |
| Buffer10X | 5.0 | 5.0 | 5.0 |
| MnCl$_2$ (10 mM) | — | 0.75 | — |
| H$_2$O | 38.5 | 28.75 | 34.5 |
| Taq polymerase (5 U/μl) | 0.5 | 0.5 | 0.5 |
| Total volume: | 100 | 100 | 100 |

The temperature program described above was performed in the thermocycler mentioned above with only one 2.segment. Half of the samples (50 μl) was removed and saved on −20° C. (samples A2, B2 and C2).

With the remaining 50 μl samples the addition of the reagents and the temperature program were performed again with the same conditions as above. 50 μl of each sample were saved on −20° C. (A3, B3 and C3). The rest of them were applied to agarose (2%) gel electrophoresis to check the reaction efficiency.

All of the nine samples (A1–3, B1–3, and C1–3) were purified with High Pure™ PCR Product Purification Kit (Roche Diagnostics). With each samples the following reaction were set up:

|                        | Volume (μl) |
|------------------------|-------------|
| Sample                 | 50.0        |
| Buffer10X              | 10.0        |
| dNTP mix (10 mM each)  | 2.0         |
| Primer 1:xyIA R        | 10.0        |
| Primer 2:xyIA L        | 10.0        |
| MgCl₂                  | 10.0        |
| H₂O                    | 7.0         |
| Taq polymerase & u/μl  | 1.0         |
| Total Volume           | 100.0       |

The temperature program described above was performed in the thermocycler mentioned above with ten repeated 2.segment. The samples were purified as before and used for ligation experiments.

Example 2
Cloning and Selection of Mutant xylA Genes

The mutant xylA genes obtained in the previous example were inserted into the general cloning vector pGEM-t Easy (Promega Corp.). 300 ng of vector (pGEM-t Easy) was incubated overnight at 4° C. with 200 to 500 ng of insert in total volume of 10 μl. A control reaction without insert was also conducted.

The ligation products were transformed into *E. coli* HB101 (xylA5), which is a xylose isomerase deficient strain. HB101 High Efficiency Competent Cells (Promega Corp.) were transformed according to the suppliers recommendations, and 3×100 μl or 5×200 μl were plated on LB-agar supplemented with ampicillin (50 μl/μl) and X-gal (20 μg/μl). Colonies where moved to MacConkey-agar plates with ampicillin and xylose (2%), either with toothpicks or by replica plating. The plates were incubated at 37° C. overnight and thereafter incubated at different temperatures (37° C. and 55° C.) until the colour reaction, which indicates xylose utilisation (orange to red), was seen. On the MacConkey plates, *E. coli* DH5α (harbouring pUC18 for amp$^R$) and *E. coli* HB101 (harbouring pGEM-t Easy for amp$^R$) were used as positive and negative control, respectively. Note that the strain HB101 has Xyl⁻, whereas the strain DH5α has Xyl⁺ phenotype.

All colonies similar colour reaction (xylose utilisation) to the positive control were spread on new MacConkey-amp-xylose plates, LB-amp plates and inoculated in liquid LB-amp (50 μl/μl). Plasmid DNA from the liquid cultures were prepared using the CTAB method, and subjected to EcoRI digestion to establish if they contained the xy/A-insert. Plasmids with insert were then retransformed into *E. coli* HB101 to confirm their phenotype on MacConkey plates. Correct colonies were cultured as above and the plasmids purified with Nucleon mini plasmid DNA preparation kit (Amersham). These DNAs were used in the subsequent experiments and to determine the nucleic acid sequences of the mutated genes. Schematic representation one of the obtained plasmid is shown in FIG. 1.

Example 3
Kinetic Characterisation of the Mutant Xylose Isomerases

*E. coli* HB101 haboring plods PUSM1010, PUSM1021, pUSM1024, pTJSM1026, and pUSMwt, with the mutated and the wildtype xylose isomerase genes respectively (as described in the previous two examples) were grown at 37° C. in 50 ml LB media containing 100 μl/ml ampicillin. The cells were harvested by centrifugation in the stationary phase of growth and washed once with ice cold distilled water. Washed cells were resusprended in 100 mM triethanolamine, pH 7.0, 0.5 mg/ml lysozyme (130000 U/mg), 0.25 mg/ml DNase, and 1 mM phenylmethylsulphonyl fluoride (PMSF) in dimethylsulfoxide (DMSO). The suspensions were kept at room temperature for one hour and then on ice for two hours before being put in a freezer at −20° C. The cell lysates were thawed on ice, cell debris was removed by centrifugation (1300 rpm for 15 minutes at 4° C.) and the supernatants were used as the crude enzyme preparations.

Protein concentration was determined with the Bradford method (Bradford (1976)) using the Pierce protein reagent with bovine serum albumin as standard.

Figure 2:
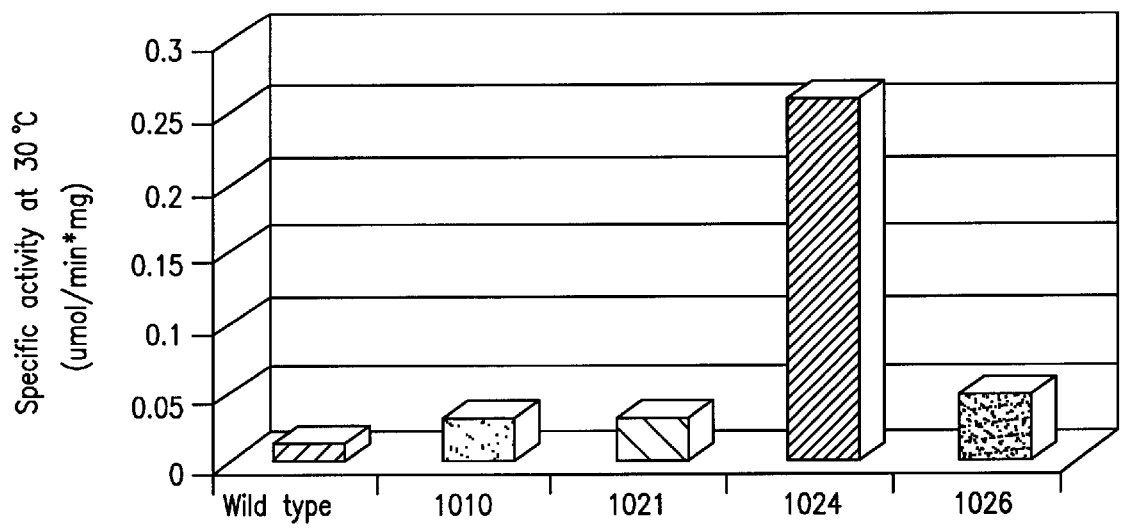

The xylose isomerase was assayed by incubating 700 mM D-xylose with suitable amount of crude enzyme preparation in the presence of 10 mM MnCl₂ and 100 mM triethanolamine, pH 7.0 at the desired temperature in 0.5 ml volume. Glucose isomerase activity was assayed under the same reaction conditions, except that D-glucose instead of xylose was used in the reaction mixture. The reaction was terminated after 10 minutes by adding 150 μl 50% trichloroaceticacid. The reaction mixture was neutralized with 185 μl 2 M Na₂CO₃. The formed xylulose or fructose was measured on a COBAS MIRA (Roche) automated spectrophotometer via enzymatic reduction with 0.04 or 0.5 units of Sorbitol Dehydrogenase (purchased from Roche), respectively in the presence of 0.15 mM NADH at pH 7.0, 37° C. in 200 μl reaction volume. The rate of disappearance of NADH was followed at 340 nm and the concentration of D-xylulose or D-fructose was calculated using calibration curves. One unit of xylose (glucose) isomerase activity was defined as the amount of crude enzyme needed to produce 1 μmol of product per minute under the assay conditions. The specific activity (U min$^{-1}$ mg$^{-1}$) was determined from the activity and the protein concentration of the crude enzyme preparations. Comparison between the specific activities at 30° C. is shown in FIG. 2 and Table 1. The change of the specific activity with the temperature for each enzyme is displayed in FIG. 3. The temperature optimum for the mutants were roughly the same as for the wild type enzyme except for mutant 1021, which had ~10° C. lower temperature optimum.

TABLE 1

| mutant    | $V_{max}$ (μmol/min$^{-1}$mg$^{-1}$) at 30° C. |
|-----------|------------------------------------------------|
| M1026     | 0.048                                          |
| M1024     | 0.261                                          |
| M1021     | 0.035                                          |
| M1010     | 0.031                                          |
| wild type | 0.014                                          |

The kinetic parameters $V_{max}$ (μmol min$^{-1}$ mg$^{-1}$) and $K_m$ (mM) were determined from Michaelis-Menten plots of specific activities at various substrate concentrations by nonlinear regression analysis with Sigma Plot (SSPS Inc.) software. Typically, duplicate measurements were used to determine the $K_m$ value at 6–10 concentrations of the substrate, with a concentration range covering the value of $K_m$.

The inhibition constant for xylitol ($K_i$) was determined by incubating the crude enzyme preparations with different xylose concentrations (20–400 mM) at different fixed xylitol concentrations. The mutants had a higher Ki for xylitol, which is an inhibitor to xylose isomerase, compared to the wildtype enzyme.

The effect of pH on the activity of the enzymes was followed in the pH range 5–10 in a buffer prepared by mixing acetate, piperazine-N,N'-bis-(2-ethanolsulphonic acid) (PIPES), N-2-hydroxyehylpiperazine-N'-2-etanesulfnicacid (HEPES) and glycine at final concentration 50 mM each as described by (Dekker at al. (1992) Appl. Mirobiol.

Figure 4:
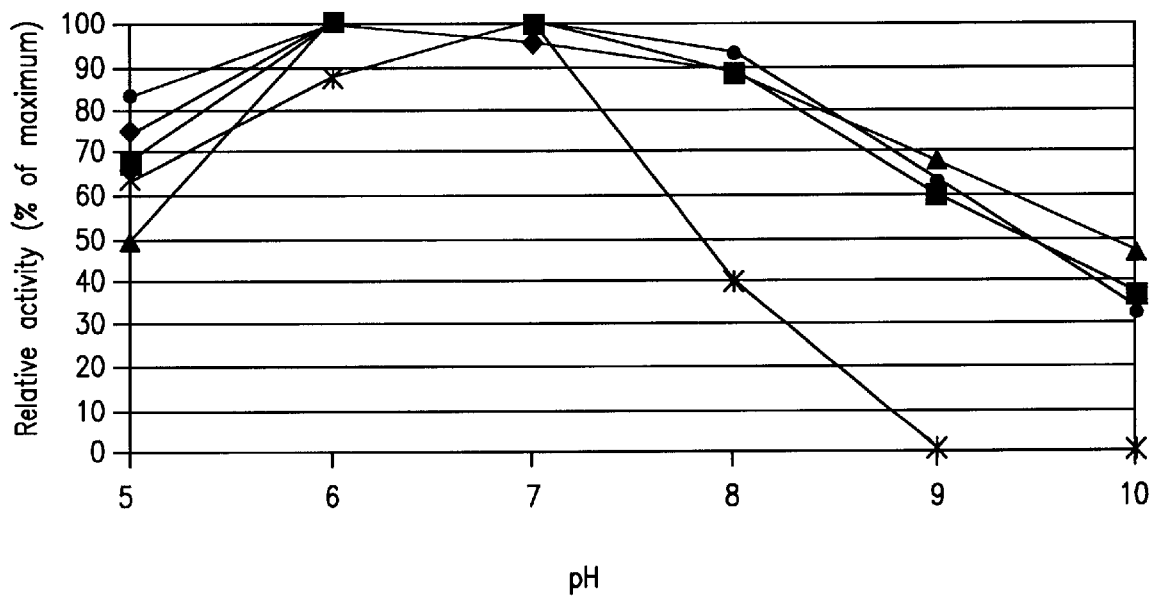

Biotechnol. 36: 727–732). The pH was adjusted at 60° C. with NaOH. The assay was performed at 60° C. in mixture containing 700 mM D-xylose 10 mM $MnCl_2$. Above pH 7.0 corrections were made for the chemical isomerisation of D-xylose. The change of the specific activity with the pH for each enzyme is shown in FIG. 4. The mutated xylose isomerases all had a broader pH range than the wildtype, but the same pH optimum ~7.0. Thermal stability of wild type xylose isomerases and mutated xylose isomerases where tested by incubating metal free enzyme preparations at 70° C. in 200 mM triethanolamine, pH7.0, 10 mM $MnCl_2$. Residual activities of timed aliquots were recorded using xylose as substrate.

Table 2 illustrates a summary of the catalytic properties of the tested mutated xylose isomerases and the wild type xylose isomerase.

TABLE 2

Catalytic properties of mutated xylose isomerases and the wild type xylose isomerase.

| | Mutant 1010 | Mutant 1021 | Mutant 1024 | Mutant 1026 | Wildtype |
|---|---|---|---|---|---|
| pH optimum | 6–8 | 6–8 | 6–8 | 6–8 | 6–7.5 |
| Temp. optimum (° C.) | 85 | 70–80 | 90 | 90 | 85 |
| Vmax xylose ($\mu$mole/min *mg) | $0.44 \pm 1.8*10^{-2}$ | $0.84 \pm 2.9*10^{-2}$ | $3.08 \pm 8.8*10^{-2}$ | $0.92 \pm 2.4*10^{-2}$ | $0.043 \pm 8.3*10^{-4}$ |
| Km xylose (mM) | 16.6 ± 2.2 | 25.1 ± 4.0 | 89.4 ± 8.4 | 28.7 ± 3.3 | 3.44 ± 0.4 |
| Vmax glucose ($\mu$mole/min *mg) | $0.0034 \pm 8.4*10^{-3}$ | $0.13 \pm 3.1*10^{-3}$ | $0.54 \pm 2.6*10^{-2}$ | $0.18 \pm 6.7*10^{-3}$ | $0.015 \pm 5.2*10^{-4}$ |
| Km glucose (mM) | 139.9 ± 8.1 | 52.0 ± 4.9 | 130.8 ± 17.1 | 171.8 ± 10.0 | 146.8 ± 12.3 |
| Ki xylitol (mM) | 10.1 | 33.2 | 1174 | 68.7 | 4.6 |

Furthermore, the effect of different bivalent cations (10 mM) on the activity of EDTA treated enzymes was investigated. The specific activity with 10 mM $MnCl_2$ at 60° C. was set to 100% for each enzyme. The results are shown in table 3.

TABLE 3

Effect of different bivalent cations (10 mM) on the activity of EDTA treated enzymes

| Enzyme | $Co^{2+}$ (% relative activity) | $Mg^{2+}$ (% relative activity) |
|---|---|---|
| Mutant 1010 | 22.9 | 51.6 |
| Mutant 1021 | 7.4 | 23.2 |
| Mutant 1024 | 33.6 | 22.7 |
| Mutant 1026 | 34.6 | 38.9 |
| Wild type | 87.9 | 73.8 |

Example 4
Construction of Yeast Expression Vector

The vector pMA91 (Mellor et al. (1983)) was hydrolysed with the restriction enzyme HindIII (Roche) to obtain the yeast PGK1 promoter and terminator sequences. The digested DNA was electrophorised on 1.0 % agarose gel and the 1.8 kb fragment was cut out from the gel with a scalpel. The DNA fragment was recovered from the agarose slice with the QIAqiuck Gel extraction kit (QIAGEN). YEplac112 (Gietz and Sugino (1988)) was linearised with HindIII, digested with Shrimp Alkaline Phosphatase (Roche) and purified with QlAquick PCR purification kit (QIAGEN). The two DNA fragments were ligated using T4 DNA ligase (Gibco BRL) according to the supplier's recommendations. Ligation products were transformed into *E. coli* HB101 and plated onto LB agar plates with 100 $\mu$g/ml ampicillin. The plates were incubated overnight on 37° C., 5 colonies were picked up and inoculated into 5 ml LB media with 100 $\mu$g/ml ampicillin. The cultures were incubated overnight on 37° C. with rocking. Plasmids were isolated with QIAprep Spin kit (QIAGEN) and used for restriction analysis. One isolate showing the correct HindIII digestion pattern was chosen and it was inoculated into 100 ml LB media with 100 $\mu$g/ml ampicillin. The culture was grown overnight on 37° C. with 200 rpm shaking. Large scale plasmid preparation was performed with QIAGEN MAXIPREP (QIAGEN) and the obtained plasmid (in the following referred as YEplacPGK) was used in the following experiment. pUSM1026 was transformed into *E coli* GM2163 (dam⁻) and plated onto LB agar with 100 $\mu$l/ml ampicillin and 10 $\mu$g/ml chloramphenicol. A colony was inoculated into 5–10 ml LB with 100 $\mu$g/ml ampicillin and 10 $\mu$g/ml chloramphenicol. The culture was grown overnight on 37° C. with rocking. Unmethylated plasmid was isolated from the culture with Quantum Prep plasmid miniprep kit (BIO-RAD). The plasmid was cut with BclI (Roche) on 50° C. and applied to a 1.0% agarose gel. The 1.2 kb fragment was cleaved out with a scalpel and purified from the agarose gel with QlAquick Gel extraction kit (QIAGEN). 1–5 $\mu$g of YEplacPGK was digested with BglII (Roche), dephosphorilated with Shrimp Alkaline Phosphatase (Roche) and purified with QlAquick PCR purification kit (QIAGEN). The two DNA fragments were mixed and ligated with T4 DNA ligase (Gibco BRL) under the conditions recommended by the manufacturer. The ligation mixture was transformed into *E. coli* and plated onto LBagar with 100 $\mu$g/ml ampicillin. 8–10 colonies were picked and inoculated into 5–10 ml LB+100 $\mu$g/ml ampicillin. After the cultures had grown overnight on 37° C. with rocking, plasmids were isolated with Quantum Prep plasmid miniprep (BIO-RAD). The plasmids were sequenced to determine the direction of the insert compared to the promoter. One preparatum with the correct sequence was chosen to be used in the subsequent experiments and named M1026.

Figure 5:
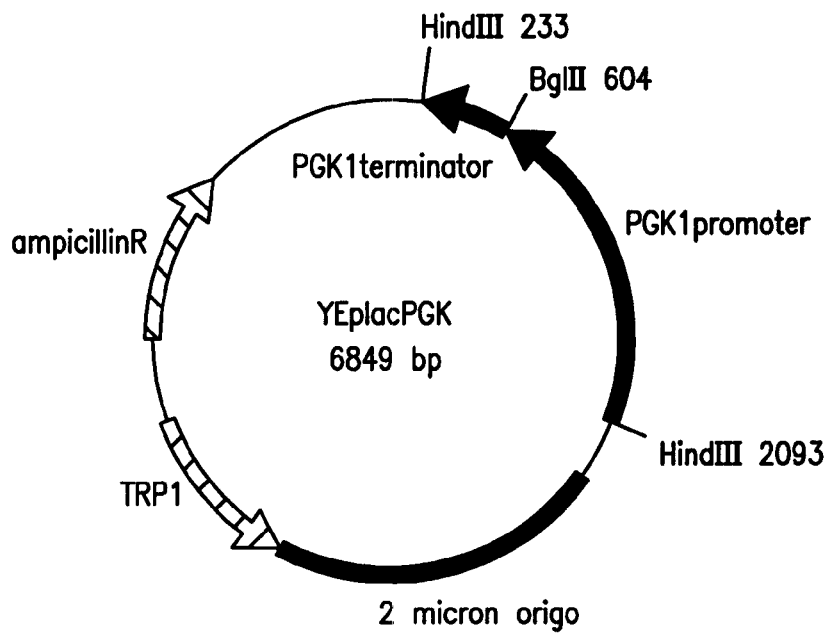
Figure 5:
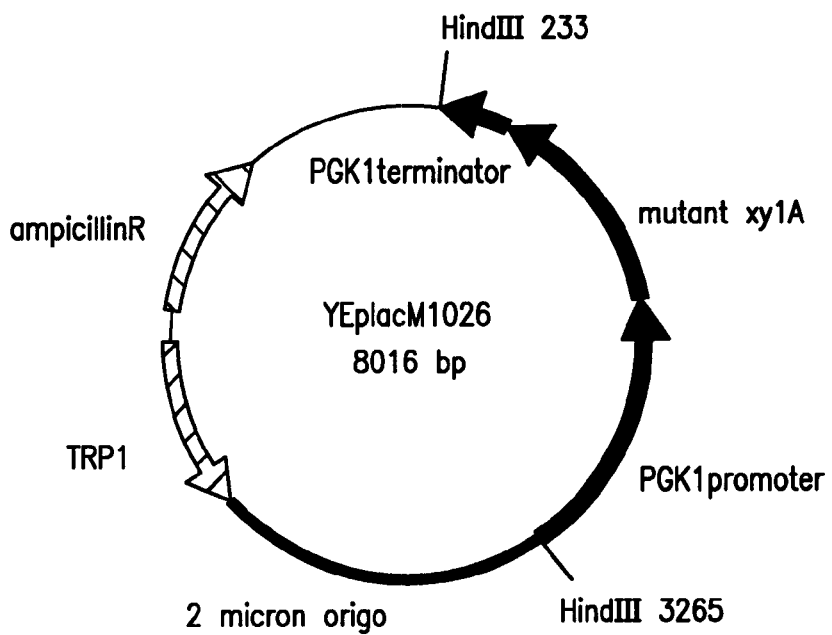

To construct a control plasmid similar to the one above, but containing the wild type xylA gene, the plasmid pBXI (Walfridsson et al. (1986)) was partially hydrolysed with HindIII (Roche). After separating the fragments on 0.7% agarose gel the 3.0 kb fragment was cut out and purified with QlAquick Gel extraction kit (QIAGEN). The fragment carrying the promoter-gene-terminator cassette was inserted into YEplac112, which was linearised with HindIII and dephosphorilated before. The ligation products were transformed into *E. coli* and plasmids were reisolated from 3 colonies, as described above. An isolate showing the expected restriction pattern with HindIII was used in the following experiments and named YEplacTthXI. The constructed yeast expression plasmids are shown in FIG. 5 (YEplacPGK, YEplacM1026) and FIG. 6. (YEplacTthXI).

Example 5
Expression of the Mutant xylA in Saccharomyces cerevisiae

Plasmids YEplacPGK, YEplacM1026 and YEplacTthXI were transformed into *Saccharomyces cerevisiae* CEN.PK2-1D with the method of (Gietz and Woods (1994)). The transformants were plated onto SC-Trp plates and incubated on 30° C. for 2 days. Transformants were inoculated into 5 ml SC-Trp media and were grown overnight on 30° C. with rocking. The cells were harvested by centrifugation (10 minutes, 5000 g), suspended in distilled water and centrifuged again. The cell pellets were suspended in 500 μl Y-PER reagent (Pierce) supplemented with 1 mM phenylmethylsulfonyl fluoride. The extraction was performed on room temperature for 30 minutes with shaking. After removing the cell debris by centrifugation for 5 minutes at 13000 g, the resulting supernatants were used for determining the xylose isomerase activity. The xylose isomerase assay and the protein concentration measurements were as described in Example 3.

TABLE 4

Xylose isomerase specific activities in recombinant *S. cerevisiae* strains.

| S. cerevisiae transformed with: | YEplacPGK | YEplacM1026 | YEplacTthXI |
|---|---|---|---|
| Xylose isomerase specific activity: | <0.01 | 0.59 ± 0.017 | 0.49 ± 0.009 |

LEGENDS TO FIGURES

FIG. 1. Schematic representation of the plasmid pUSM1026

FIG. 2. Specific activities of the mutated xylose isomerases and the wildtype xylose isomerase at 30° C.

Figure 3:
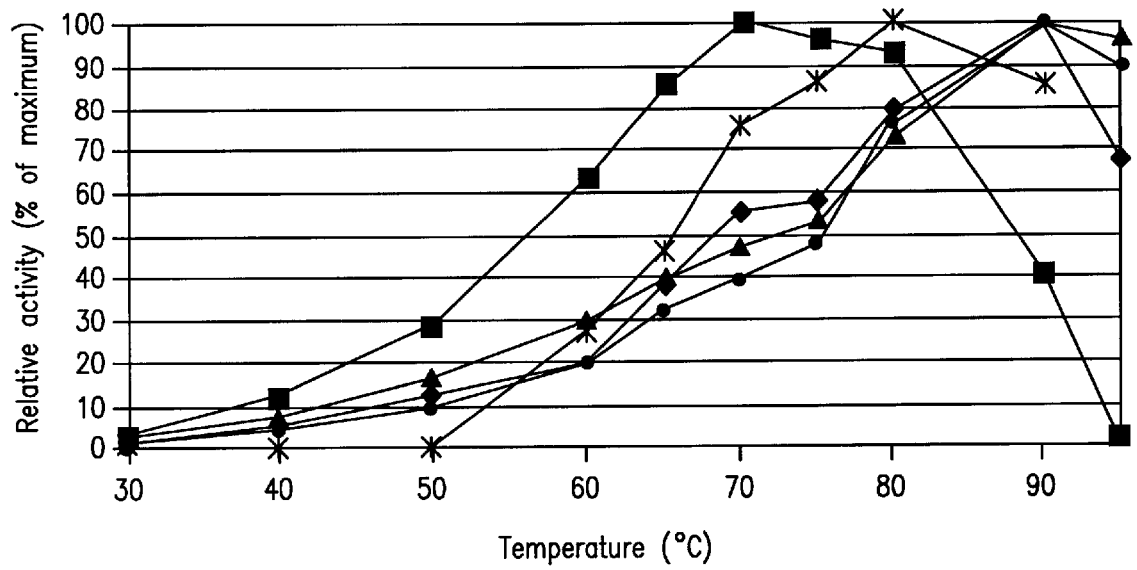

FIG. 3. The relative activity of the mutated xylose isomerases and the wildtype xylose isomerase at different temperatures: (◆) mutant 1010, (-) mutant 1021, (□) mutant 1024, (⌒) mutant 1026, (*) wildtype. The scale of relative activity (%) indicates the percentage of experimental value at various temperature relative to the maximum value of each enzyme.

FIG. 4. The relative activity of the mutant xylose isomerases and the wildtype xylose isomerase at different pH: (◆) mutant 1010, (-) mutant 1021, (□) mutant 1024, (⌒) mutant 1026, (*) wildtype. The scale of relative activity (%) indicates the percentage of experimental value at various pH relative to the maximum value of each enzyme.

FIG. 5: Yeast expression vectors transformed into *S. cerevisiae*.

Figure 6:
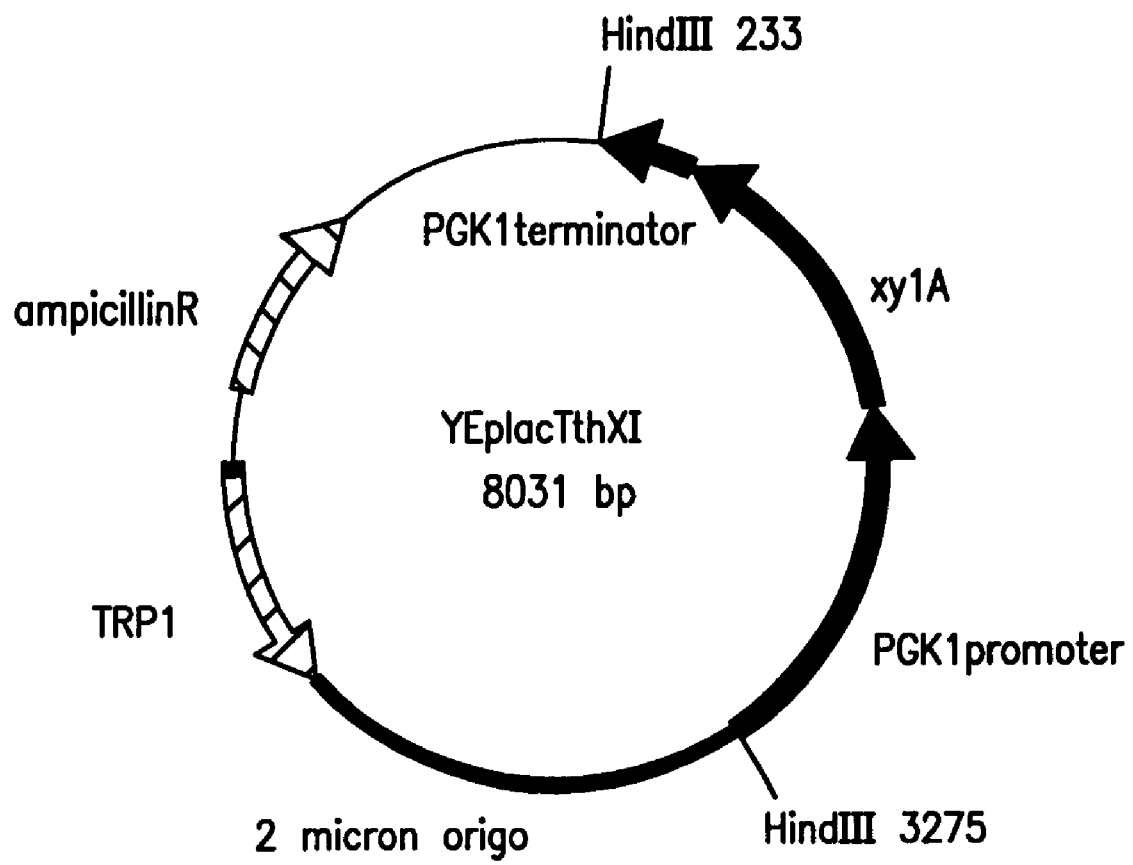

FIG. 6: Map of yeast expression plasmid YEplacTthXI.

REFERENCES

1. Amore et al. (1989) Appl. Microbiol. Biotechnol 30: 351–357
2. Bradford (1976) Anal. Biochem. 72: 248–254
3. Dekker et al. (1992) Appl. Mirobiol. Biotechnol. 36: 727–732
4. Gietz and Sugino (1988) Gene 74: 527–534.
5. Gietz and Woods (1994) Molecular Genetics of Yeast: Practical Approaches, ed. J. A. Johnston, Oxford University Press pp. 121–134.
6. Godfrey and Reichelt (1983) Industrial enzymology: The application of enzymes in industry. The Nature Press, New York, pp. 375–388
7. Huang, X. and W. Miller. Adv. Appl. Math. (1991) 12:337–357
8. Kuhn et al. (1995) Appl. Environ. Microbiol. 61:1580–1585]
9. Mellor et al. (1983) Gene 24: 1–14
10. Moes et al. (1996) Biotechnol. Lett. 8: 269–274
11. Pearson W. R and D. J. Lipman (1988) PNAS USA 85:2444–2448
12. Richard et al (1999) FEBS Lett. 457: 135–138
13. Sambrook et al. (1989) Molecular Cloning: A Laboratory Manual
14. Sarthy et al. (1987) Appl. Environ. Microbiol. 53: 1996–2000
15. Tantirungkij et al. (1993) J. Ferment. Bioeng. 75: 83–88.
16. Walfridsson et al. (1996) Appl. Environ. Microbiol. 62: 4648–4651
17. Yamanaka (1969) Arch. Bochem. Biophys. 131: 502–506.

---

What is claimed is:

1. An isolated nucleic acid encoding a polypeptide comprising an amino acid sequence encoded by SEQ. ID. No. 1,
wherein nnn at nucleotides 487–489 of SEQ. ID. No. 1 encodes any amino acid, and nnn at nucleotides 1114–1116 of SEQ. ID. No. 1 encodes any nucleotide except glutamic acid, and
wherein said polypeptide has at least 10% higher specific xylose isomerase activity than a xylose isomerase encoded by SEQ ID No. 2.

2. The isolated nucleic acid of claim 1, wherein said polypeptide has at least 10% higher specific xylose isomerase activity than the xylose isomerase encoded by SEQ. ID. No. 2 at mesophilic temperatures.

3. The isolated nucleic acid of claim 1, wherein said polypeptide has at least 10% higher specific xylose isomerase activity than the xylose isomerase encoded by SEQ. ID. No. 2 at temperatures above 80° C.

4. The isolated nucleic acid of claim 1, wherein said polypeptide has at least 10% higher specific xylose isomerase activity than the xylose isomerase encoded by SEQ. ID. No. 2 at a pH lower than 7.5.

5. The isolated nucleic acid of claim 1, wherein said polypeptide has at least 10% higher specific xylose isomerase activity than the xylose isomerase encoded by SEQ. ID. No. 2 in the presence of xylitol.

6. The isolated nucleic acid of claim 1, wherein said nnn at nucleotides 487–489 of SEQ. ID. No. 1 encodes leucine.

7. The isolated nucleic acid of claim 1, wherein nnn at nucleotides 1114–1116 of SEQ. ID. No. 1 encodes glycine.

8. The isolated nucleic acid of claim 1, wherein nnn at nucleotides 487–489 of SEQ. ID. No. 1 encodes phenylalanine.

9. The isolated nucleic acid of claim 8, wherein said nnn at nucleotides 1114–1116 of SEQ. ID. No. 1 encodes glycine.

10. The isolated nucleic acid of claim 1, wherein nnn at nucleotides 487–489 of SEQ. ID. No. 1 encodes leucine.

11. The isolated nucleic acid of claim 10, wherein said nnn at nucleotides 1114–1116 of SEQ. ID. No. 1 encodes glycine.

12. The isolated nucleic acid of claim 1, wherein said nucleic acid comprises a nucleotide sequence selected from the group consisting of SEQ. ID. No. 3, SEQ. ID. No. 5, SEQ. ID. No. 7, and SEQ. ID. No. 9.

13. The isolated nucleic acid of claim 1, wherein said nucleic acid is selected from the group consisting of DNA, RNA, and PNA.

14. The isolated nucleic acid of claim 1, wherein said nucleic acid is DNA.

15. An isolated nucleic acid having a nucleotide sequence that is at least 85%, but less than 100%, identical to the nucleotide sequence of SEQ. ID. No. 2,
wherein said isolated nucleic acid encodes a polypeptide having xylose isomerase activity,
wherein said polypeptide has at least 10% higher specific xylose isomerase activity than the xylose isomerase encoded by SEQ. ID. No. 2, and
wherein said isolated nucleic acid is mutated, with respect to SEQ. ID. No. 2, such that nucleotide codon 1114–1116 encodes any amino acid except glutamic acid.

16. A vector comprising the isolated nucleic acid of claim 15.

17. A cell comprising the vector of claim 16.

18. The cell of claim 17, which is a yeast cell.

19. The yeast cell of claim 18, wherein said yeast cell is from a species selected from the group consisting of Pichia, Candida, Schizosaccharomyces, Zygosaccharomyces, and Saccharomyces.

20. The yeast cell of claim 19, wherein said cell is selected from the group consisting of *Saccharomyces cerevisiae, Saccharomyces bayanus,* and *Saccharomyces carlsbergensis.*

21. The yeast cell of claim 20, wherein said cell is a *Saccharomyces cerevisiae.*

22. A vector comprising the isolated nucleic acid of claim 1.

23. A cell comprising the vector of claim 22.

24. The cell of claim 23, which is a yeast cell.

25. The yeast cell of claim 24, wherein said yeast cell is from a species selected from the group consisting of Pichia, Candida, Schizosaccharomyces, Zygosaccharomyces, and Saccharomyces.

26. The yeast cell of claim 25, wherein said cell is selected from the group consisting of *Saccharomyces cerevisiae, Saccharomyces bayanus,* and *Saccharomyces carlsbergensis.*

27. The yeast cell of claim 26, wherein said cell is a *Saccharomyces cerevisiae.*

28. A process for producing ethanol, wherein said process comprises:
   a) contacting at least one cell of claim 23 with a substrate that contains one or more carbon sources selected from xylose and polymerized xylose moieties;
   b) culturing said at least one cell under conditions where isomerization of D-xylose to D-xylulose occurs and the D-xylulose is catabolized to ethanol; and
   c) optionally, recovering the ethanol.

29. A process for producing a polypeptide having an amino acid sequence comprising a sequence selected from the group consisting of SEQ. ID. No. 4, SEQ. ID. No. 6, SEQ. ID. No. 8, and SEQ. ID. No. 10, wherein said process comprises transcribing and translating at least a portion of the isolated nucleic acid of claim 1.

* * * * *

SEQUENCE LISTING

```
<160> NUMBER OF SEQ ID NOS: 12

<210> SEQ ID NO 1
<211> LENGTH: 1164
<212> TYPE: DNA
<213> ORGANISM: Thermus thermophilus
<220> FEATURE:
<221> NAME/KEY: variation
<222> LOCATION: (487)..(489)
<223> OTHER INFORMATION: nnn represents a codon coding for any amino
      acid
<221> NAME/KEY: variation
<222> LOCATION: (1114)..(1116)
<223> OTHER INFORMATION: nnn represents a codon coding for any amino
      acid except glutamate

<400> SEQUENCE: 1
atgtacgagc ctaaaccgga gcacaggttt acctttggcc tttggactgt gggcaatgtg      60
ggccgtgatc ccttcgggga cgcggttcgg gagaggctgg acccggttta cgtggttcat     120
```

-continued

```
aagctggcgg agcttggggc ctacggggta aaccttcacg acgaggacct gatcccgcgg    180
ggcacgcctc ctcaggagcg ggaccagatc gtgaggcgct tcaagaaggc tctcgatgaa    240
accggcctca aggtccccat ggtcaccgcc aacctcttct ccgaccctgc tttcaaggac    300
ggggccttca cgagcccgga cccttgggtt cgggcctatg ccttgcggaa gagcctggag    360
accatggacc tgggggcaga gcttggggcc gagatctacg tggtctggcc gggccgggag    420
ggagctgagg tggaggccac gggcaaggcc cggaaggtct gggactgggt gcgggaggcg    480
ctgaacnnna tggccgccta cgccgaggac cagggatacg ggtaccggtt tgccctcgag    540
cccaagccta cgagccccg gggggacatt tacttcgcca ccgtggggag catgctcgcc     600
tttattcata ccctggaccg gcccgagcgc ttcggcctga accccgagtt cgcccacgag    660
accatggccg ggcttaactt tgtccacgcc gtggcccagg ctctcgacgc cgggaagctt    720
ttccacattg acctcaacga ccaacggatg agccggtttg accaggacct ccgcttcggc    780
tcggagaacc tcaaggcggc ctttttcctg gtggacctcc tggaaagctc cggctaccag    840
ggcccccgcc actttgacgc ccacgccctg cgtaccgagg acgaagaagg ggtttgggcc    900
ttcgcccgag gctgcatgcg tacctacctg atcttaaagg aaagggctga agccttccgc    960
gaggatcccg aggtcaagga gcttcttgcc gcttactatc aagaagatcc tgcggccttg    1020 gccctttttgg gcccctactc ccgcgagaag gccgaagccc tcaagcgggc ggagcttccc    1080
ctcgaggcca gcggcgccg gggttatgcc ctgnnncgcc tggaccagct ggcggtggag    1140
tacctcctgg gggtgcgggg gtga                                          1164
```

<210> SEQ ID NO 2
<211> LENGTH: 1164
<212> TYPE: DNA
<213> ORGANISM: Thermus thermophilus

<400> SEQUENCE: 2

```
atgtacgagc ctaaaccgga gcacaggttt acctttggcc tttggactgt gggcaatgtg     60
ggccgtgatc ccttcgggga cgcggttcgg gagaggctgg acccggttta cgtggttcat    120
aagctggcgg agcttggggc ctacggggta aaccttcacg acgaggacct gatcccgcgg    180
ggcacgcctc ctcaggagcg ggaccagatc gtgaggcgct tcaagaaggc tctcgatgaa    240
accggcctca aggtccccat ggtcaccgcc aacctcttct ccgaccctgc tttcaaggac    300
ggggccttca cgagcccgga cccttgggtt cgggcctatg ccttgcggaa gagcctggag    360
accatggacc tgggggcaga gcttggggcc gagatctacg tggtctggcc gggccgggag    420
ggagctgagg tggaggccac gggcaaggcc cggaaggtct gggactgggt gcgggaggcg    480
ctgaacttca tggccgccta cgccgaggac cagggatacg ggtaccggtt tgccctcgag    540
cccaagccta cgagccccg gggggacatt tacttcgcca ccgtggggag catgctcgcc     600
tttattcata ccctggaccg gcccgagcgc ttcggcctga accccgagtt cgcccacgag    660
accatggccg ggcttaactt tgtccacgcc gtggcccagg ctctcgacgc cgggaagctt    720
ttccacattg acctcaacga ccaacggatg agccggtttg accaggacct ccgcttcggc    780
tcggagaacc tcaaggcggc ctttttcctg gtggacctcc tggaaagctc cggctaccag    840
ggcccccgcc actttgacgc ccacgccctg cgtaccgagg acgaagaagg ggtttgggcc    900
ttcgcccgag gctgcatgcg tacctacctg atcttaaagg aaagggctga agccttccgc    960
gaggatcccg aggtcaagga gcttcttgcc gcttactatc aagaagatcc tgcggccttg    1020
```

-continued

```
gcccttttgg gcccctactc ccgcgagaag gccgaagccc tcaagcgggc ggagcttccc      1080
ctcgaggcca agcggcgccg gggttatgcc ctggaacgcc tggaccagct ggcggtggag      1140
tacctcctgg gggtgcgggg gtga                                             1164
```

<210> SEQ ID NO 3
<211> LENGTH: 1164
<212> TYPE: DNA
<213> ORGANISM: Thermus thermophilus

<400> SEQUENCE: 3

```
atgtacgagc ctaaaccgga gcacaggttt acctttggcc tttggactgt gggcaatgtg       60
ggccgtgatc ccttcgggga cgcggttcgg gagaggctgg acccggttta cgtggttcat      120
aagctggcgg agcttggggc ctacgggta  accttcacg acgaggacct gatcccgcgg       180
ggcacgcctc ctcaggagcg ggaccagatc gtgaggcgct tcaagaaggc tctcgatgaa      240
accggcctca aggtccccat ggtcaccgcc aacctcttct ccgaccctgc tttcaaggac      300
ggggccttca cgagcccgga cccttgggtt cgggcctatg ccttgcggaa gagcctggag      360
accatggacc tggggcaga  gcttggggcc gagatctacg tggtctggcc gggccgggag      420
ggagctgagg tggaggccac gggcaaggcc cggaaggtct gggactgggt gcgggaggcg      480
ctgaacttca tggccgccta cgccgaggac cagggatacg ggtaccggtt tgccctcgag      540
cccaagccta cgagccccg  ggggacatt  tacttcgcca ccgtggggag catgctcgcc      600
tttattcata ccctggaccg gcccgagcgc ttcggcctga ccccgagtt  cgcccacgag      660 accatggccg gcttaacctt tgtccacgcc gtggcccagg ctctcgacgc cgggaagctt      720
ttccacattg acctcaacga ccaacggatg agccggtttg accaggacct ccgcttcggc      780
tcggagaacc tcaaggcggc cttttttcctg gtggacctcc tggaaagctc cggctaccag      840
ggcccccgcc actttgacgc ccacgccctg cgtaccgagg acgaagaagg ggtttgggcc      900
ttcgcccgag gctgcatgcg tacctacctg atcttaaagg aaagggctga agccttccgc      960
gaggatcccg aggtcaagga gcttcttgcc gcttactatc aagaagatcc tgcggccttg     1020
gcccttttgg gcccctactc ccgcgagaag gccgaagccc tcaagcgggc ggagcttccc     1080
ctcgaggcca agcggcgccg gggttatgcc ctgggacgcc tggaccagct ggcggtggag     1140
tacctcctgg gggtgcgggg gtga                                            1164
```

<210> SEQ ID NO 4
<211> LENGTH: 387
<212> TYPE: PRT
<213> ORGANISM: Thermus thermophilus

<400> SEQUENCE: 4

```
Met Tyr Glu Pro Lys Pro Glu His Arg Phe Thr Phe Gly Leu Trp Thr
  1               5                  10                  15

Val Gly Asn Val Gly Arg Asp Pro Phe Gly Asp Ala Val Arg Glu Arg
                 20                  25                  30

Leu Asp Pro Val Tyr Val Val His Lys Leu Ala Glu Leu Gly Ala Tyr
             35                  40                  45

Gly Val Asn Leu His Asp Glu Asp Leu Ile Pro Arg Gly Thr Pro Pro
         50                  55                  60

Gln Glu Arg Asp Gln Ile Val Arg Arg Phe Lys Lys Ala Leu Asp Glu
 65                  70                  75                  80

Thr Gly Leu Lys Val Pro Met Val Thr Ala Asn Leu Phe Ser Asp Pro
                 85                  90                  95
```

```
Ala Phe Lys Asp Gly Ala Phe Thr Ser Pro Asp Pro Trp Val Arg Ala
            100                 105                 110
Tyr Ala Leu Arg Lys Ser Leu Glu Thr Met Asp Leu Gly Ala Glu Leu
        115                 120                 125
Gly Ala Glu Ile Tyr Val Val Trp Pro Gly Arg Glu Gly Ala Glu Val
    130                 135                 140
Glu Ala Thr Gly Lys Ala Arg Lys Val Trp Asp Trp Val Arg Glu Ala
145                 150                 155                 160
Leu Asn Phe Met Ala Ala Tyr Ala Glu Asp Gln Gly Tyr Gly Tyr Arg
                165                 170                 175
Phe Ala Leu Glu Pro Lys Pro Asn Glu Pro Arg Gly Asp Ile Tyr Phe
            180                 185                 190
Ala Thr Val Gly Ser Met Leu Ala Phe Ile His Thr Leu Asp Arg Pro
        195                 200                 205
Glu Arg Phe Gly Leu Asn Pro Glu Phe Ala His Glu Thr Met Ala Gly
    210                 215                 220
Leu Asn Phe Val His Ala Val Ala Gln Ala Leu Asp Ala Gly Lys Leu
225                 230                 235                 240
Phe His Ile Asp Leu Asn Asp Gln Arg Met Ser Arg Phe Asp Gln Asp
                245                 250                 255
Leu Arg Phe Gly Ser Glu Asn Leu Lys Ala Ala Phe Phe Leu Val Asp
            260                 265                 270
Leu Leu Glu Ser Ser Gly Tyr Gln Gly Pro Arg His Phe Asp Ala His
        275                 280                 285
Ala Leu Arg Thr Glu Asp Glu Glu Gly Val Trp Ala Phe Ala Arg Gly
    290                 295                 300
Cys Met Arg Thr Tyr Leu Ile Leu Lys Glu Arg Ala Glu Ala Phe Arg
305                 310                 315                 320
Glu Asp Pro Glu Val Lys Glu Leu Leu Ala Tyr Tyr Gln Glu Asp
                325                 330                 335
Pro Ala Ala Leu Ala Leu Leu Gly Pro Tyr Ser Arg Glu Lys Ala Glu
            340                 345                 350
Ala Leu Lys Arg Ala Glu Leu Pro Leu Glu Ala Lys Arg Arg Arg Gly
        355                 360                 365
Tyr Ala Leu Gly Arg Leu Asp Gln Leu Ala Val Glu Tyr Leu Leu Gly
    370                 375                 380
Val Arg Gly
385

<210> SEQ ID NO 5
<211> LENGTH: 1164
<212> TYPE: DNA
<213> ORGANISM: Thermus thermophilus

<400> SEQUENCE: 5
atgtacgagc ctaaaccgga gcacaggttt acctttggcc tttggactgt gggcaatgtg      60
ggccgtgatc ccttcgggga cgcggttcgg gagaggctgg acccggttta cgtggttcat     120
aagctggcgg agcttgggc ctacgggta aaccttcacg acgaggacct gatcccgcgg       180
ggcacgcctc ctcaggagcg ggaccagatc gtgaggcgct tcaagaaggc tctcgatgaa     240
accggcctca aggtccccat ggtcaccgcc aacctcttct ccgaccctgc tttcaaggac     300
ggggccttca cgagcccgga cccttgggtt cgggcctatg ccttgcggaa gagcctggag     360
accatggacc tggggcagag cttggggcc gagatctacg tggtctggcc gggccgggag      420
```

```
ggagctgagg tggaggccac gggcaaggcc cggaaggtct gggactgggt gcgggaggcg    480
ctgaacctca tggccgccta cgccgaggac cagggatacg ggtaccggtt tgccctcgag    540
cccaagccta acgagccccg ggggacatt tacttcgcca ccgtggggag catgctcgcc    600
tttattcata ccctggaccg gcccgagcgc ttcggcctga accccgagtt cgcccacgag    660
accatggccg ggcttaactt tgtccacgcc gtggcccagg ctctcgacgc cgggaagctt    720
ttccacattg acctcaacga ccaacggatg agccggtttg accaggacct ccgcttcggc    780
tcggagaacc tcaaggcggc cttttcctg gtggacctcc tggaaagctc cggctaccag    840 ggccccgcc actttgacgc ccacgccctg cgtaccgagg acgaagaagg ggtttgggcc    900
ttcgcccgag gctgcatgcg tacctacctg atcttaaagg aaagggctga agccttccgc    960
gaggatcccg aggtcaagga gcttcttgcc gcttactatc aagaagatcc tgcggccttg   1020
gcccttttgg gcccctactc ccgcgagaag gccgaagccc tcaagcgggc ggagcttccc   1080
ctcgaggcca agcggcgccg gggttatgcc ctgggacgcc tggaccagct ggcggtggag   1140
tacctcctgg gggtgcgggg gtga                                         1164
```

<210> SEQ ID NO 6
<211> LENGTH: 387
<212> TYPE: PRT
<213> ORGANISM: Thermus thermophilus

<400> SEQUENCE: 6

```
Met Tyr Glu Pro Lys Pro Glu His Arg Phe Thr Gly Leu Trp Thr
  1               5                  10                  15

Val Gly Asn Val Gly Arg Asp Pro Phe Gly Asp Ala Val Arg Glu Arg
             20                  25                  30

Leu Asp Pro Val Tyr Val Val His Lys Leu Ala Glu Leu Gly Ala Tyr
         35                  40                  45

Gly Val Asn Leu His Asp Glu Asp Leu Ile Pro Arg Gly Thr Pro Pro
     50                  55                  60

Gln Glu Arg Asp Gln Ile Val Arg Arg Phe Lys Lys Ala Leu Asp Glu
 65                  70                  75                  80

Thr Gly Leu Lys Val Pro Met Val Thr Ala Asn Leu Phe Ser Asp Pro
                 85                  90                  95

Ala Phe Lys Asp Gly Ala Phe Thr Ser Pro Asp Pro Trp Val Arg Ala
            100                 105                 110

Tyr Ala Leu Arg Lys Ser Leu Glu Thr Met Asp Leu Gly Ala Glu Leu
        115                 120                 125

Gly Ala Glu Ile Tyr Val Val Trp Pro Gly Arg Glu Gly Ala Glu Val
    130                 135                 140

Glu Ala Thr Gly Lys Ala Arg Lys Val Trp Asp Trp Val Arg Glu Ala
145                 150                 155                 160

Leu Asn Leu Met Ala Ala Tyr Ala Glu Asp Gln Gly Tyr Gly Tyr Arg
                165                 170                 175

Phe Ala Leu Glu Pro Lys Pro Asn Glu Pro Arg Gly Asp Ile Tyr Phe
            180                 185                 190

Ala Thr Val Gly Ser Met Leu Ala Phe Ile His Thr Leu Asp Arg Pro
        195                 200                 205

Glu Arg Phe Gly Leu Asn Pro Glu Phe Ala His Glu Thr Met Ala Gly
    210                 215                 220

Leu Asn Phe Val His Ala Val Ala Gln Ala Leu Asp Ala Gly Lys Leu
225                 230                 235                 240
```

-continued

```
Phe His Ile Asp Leu Asn Asp Gln Arg Met Ser Arg Phe Asp Gln Asp
                245                 250                 255

Leu Arg Phe Gly Ser Glu Asn Leu Lys Ala Ala Phe Phe Leu Val Asp
            260                 265                 270

Leu Leu Glu Ser Ser Gly Tyr Gln Gly Pro Arg His Phe Asp Ala His
        275                 280                 285

Ala Leu Arg Thr Glu Asp Glu Gly Val Trp Ala Phe Ala Arg Gly
    290                 295                 300

Cys Met Arg Thr Tyr Leu Ile Leu Lys Glu Arg Ala Glu Ala Phe Arg
305                 310                 315                 320

Glu Asp Pro Glu Val Lys Glu Leu Leu Ala Ala Tyr Tyr Gln Glu Asp
                325                 330                 335

Pro Ala Ala Leu Ala Leu Leu Gly Pro Tyr Ser Arg Glu Lys Ala Glu
            340                 345                 350

Ala Leu Lys Arg Ala Glu Leu Pro Leu Glu Ala Lys Arg Arg Arg Gly
        355                 360                 365

Tyr Ala Leu Gly Arg Leu Asp Gln Leu Ala Val Glu Tyr Leu Leu Gly
    370                 375                 380

Val Arg Gly
385
```

<210> SEQ ID NO 7
<211> LENGTH: 1164
<212> TYPE: DNA
<213> ORGANISM: Thermus thermophilus

<400> SEQUENCE: 7

```
atgtacgagc ctaaaccgga gcacaggttt acctttggcc tttggactgt gggcaatgtg      60
ggccgtgatc ccttcgggga cgcggttcgg gagaggctgg acccggttta cgtggttcat     120
aagctggcgg agcttggggc ctacgggta  aaccttcacg acgaggacct gatcccgcgg     180
ggcacgcctc ctcaggagcg ggaccagatc gtgaggcgct tcaagaaggc tctcgatgaa     240
accggcctca aggtccccat ggtcaccgcc aacctcttct ccgaccctgc tttcaaggac     300
ggggccttca cgagcccgga cccttgggtt cgggcctatg ccttgcggaa gagcctggag     360
accatggacc tggggcaga  gcttggggcc gagatctacg tggtctggcc gggccgggag     420
ggagctgagg tggaggccac gggcaaggcc cggaaggtct gggactgggt gcgggaggcg     480
ctgaacttca tggccgccta cgccgaggac cagggatacg ggtaccggtt tgccctcgag     540
cccaagccta cgagccccg  gggggacatt tacttcgcca ccgtggggag catgctcgcc     600
tttattcata ccctggaccg gcccgagcgc ttcggcctga accccgagtt cgcccacgag     660
accatggccg ggcttaactt tgtccacgcc gtggcccagg ctctcgacgc cgggaagctt     720
ttccacattg acctcaacga ccaacggatg agccggtttg accaggacct ccgcttcggc     780
tcggagaacc tcaaggcggc cttttttcctg gtggacctcc tggaaagctc cggctaccag     840
ggccccgcc  actttgacgc ccacgccctg cgtaccgagg acgaagaagg gtttggggcc     900
ttcgcccgag gctgcatgcg tacctacctg atcttaaagg aaagggctga agccttccgc     960
gaggatcccg aggtcaagga gcttcttgcc gcttactatc aagaagatcc tgcggccttg    1020
gcccttttgg gcccctactc ccgcgagaag gccgaagccc tcaagcgggc ggagcttccc    1080
ctcgaggcca agcggcgccg gggttatgcc ctggacgcc  tggaccagct ggcggcggag    1140
tacctcctgg gggtgcgggg gtga                                           1164
```

<210> SEQ ID NO 8
<211> LENGTH: 387
<212> TYPE: PRT
<213> ORGANISM: Thermus thermophilus

<400> SEQUENCE: 8

Met Tyr Glu Pro Lys Pro Glu His Arg Phe Thr Phe Gly Leu Trp Thr
 1               5                  10                  15

Val Gly Asn Val Gly Arg Asp Pro Phe Gly Asp Ala Val Arg Glu Arg
            20                  25                  30

Leu Asp Pro Val Tyr Val Val His Lys Leu Ala Glu Leu Gly Ala Tyr
        35                  40                  45

Gly Val Asn Leu His Asp Glu Asp Leu Ile Pro Arg Gly Thr Pro Pro
    50                  55                  60

Gln Glu Arg Asp Gln Ile Val Arg Arg Phe Lys Lys Ala Leu Asp Glu
65                  70                  75                  80

Thr Gly Leu Lys Val Pro Met Val Thr Ala Asn Leu Phe Ser Asp Pro
                85                  90                  95

Ala Phe Lys Asp Gly Ala Phe Thr Ser Pro Asp Pro Trp Val Arg Ala
            100                 105                 110

Tyr Ala Leu Arg Lys Ser Leu Glu Thr Met Asp Leu Gly Ala Glu Leu
        115                 120                 125

Gly Ala Glu Ile Tyr Val Val Trp Pro Gly Arg Glu Gly Ala Glu Val
    130                 135                 140

Glu Ala Thr Gly Lys Ala Arg Lys Val Trp Asp Trp Val Arg Glu Ala
145                 150                 155                 160

Leu Asn Phe Met Ala Ala Tyr Ala Glu Asp Gln Gly Tyr Gly Tyr Arg
                165                 170                 175

Phe Ala Leu Glu Pro Lys Pro Asn Glu Pro Arg Gly Asp Ile Tyr Phe
            180                 185                 190

Ala Thr Val Gly Ser Met Leu Ala Phe Ile His Thr Leu Asp Arg Pro
        195                 200                 205

Glu Arg Phe Gly Leu Asn Pro Glu Phe Ala His Glu Thr Met Ala Gly
    210                 215                 220

Leu Asn Phe Val His Ala Val Ala Gln Ala Leu Asp Ala Gly Lys Leu
225                 230                 235                 240

Phe His Ile Asp Leu Asn Asp Gln Arg Met Ser Arg Phe Asp Gln Asp
                245                 250                 255

Leu Arg Phe Gly Ser Glu Asn Leu Lys Ala Ala Phe Phe Leu Val Asp
            260                 265                 270

Leu Leu Glu Ser Ser Gly Tyr Gln Gly Pro Arg His Phe Asp Ala His
        275                 280                 285

Ala Leu Arg Thr Glu Asp Glu Glu Gly Val Trp Ala Phe Ala Arg Gly
    290                 295                 300

Cys Met Arg Thr Tyr Leu Ile Leu Lys Glu Arg Ala Glu Ala Phe Arg
305                 310                 315                 320

Glu Asp Pro Glu Val Lys Glu Leu Leu Ala Ala Tyr Tyr Gln Glu Asp
                325                 330                 335

Pro Ala Ala Leu Ala Leu Leu Gly Pro Tyr Ser Arg Glu Lys Ala Glu
            340                 345                 350

Ala Leu Lys Arg Ala Glu Leu Pro Leu Glu Ala Lys Arg Arg Arg Gly
        355                 360                 365

Tyr Ala Leu Gly Arg Leu Asp Gln Leu Ala Ala Glu Tyr Leu Leu Gly
    370                 375                 380

Val Arg Gly
385

<210> SEQ ID NO 9
<211> LENGTH: 1158
<212> TYPE: DNA
<213> ORGANISM: Thermus thermophilus

<400> SEQUENCE: 9

| | | | | | |
|---|---|---|---|---|---|
| atgcccaaac | cggagcacag | gtttaccttt | ggcctttgga | ctgtgggcaa | tgtgggccgt | 60 |
| gatcccttcg | gggacgcggt | tcgggagagg | ctggacccgg | tttacgtggt | tcataagctg | 120 |
| gcggagcttg | ggcctacgg | ggtaaaccctt | cacgacgagg | acctgatccc | gcggggcacg | 180 |
| cctcctcagg | agcgggacca | gatcgtgagg | cgcttcaaga | aggctctcga | tgaaaccggc | 240 |
| ctcaaggtcc | ccatggtcac | cgccaacctc | ttctccgacc | ctgctttcaa | ggacggggcc | 300 |
| ttcacgagcc | cggacccttg | ggttcgggcc | tatgccttgc | ggaagagcct | ggagaccatg | 360 |
| gacctggggg | cagagcttgg | ggccgagatc | tacgtggtct | ggccgggccg | ggagggagct | 420 |
| gaggtggagg | ccacgggcaa | ggcccggaag | gtctgggact | gggtgcggga | ggcgctgaac | 480 |
| ttcatggccg | cctacgccga | ggaccaggga | tacgggtacc | ggtttgccct | cgagcccaag | 540 |
| cctaacgagc | cccgggggga | catttacttc | gccaccgtgg | ggagcatgct | cgcctttatt | 600 |
| catccctgg | accggcccga | gcgcttcggc | ctgaaccccg | agttcgccca | cgagaccatg | 660 |
| gccgggctta | actttgtcca | cgccgtggcc | caggctctcg | acgccgggaa | gcttttccac | 720 |
| attgacctca | cgaccaacg | gatgagccgg | tttgaccagg | acctccgctt | cggctcggag | 780 |
| aacctcaagg | cggccttttt | cctggtggac | ctcctgaaaa | gctccggcta | ccagggcccc | 840 |
| cgccactttg | acgcccacgc | cctgcgtacc | gaggacgaag | aagggggtttg | ggccttcgcc | 900 |
| cgaggctgca | tgcgtaccta | cctgatctta | aaggaaaggg | ctgaagcctt | ccgcgaggat | 960 |
| cccgaggtca | aggagcttct | tgccgcttac | tatcaagaag | atcctgcggc | cttggccctt | 1020 |
| ttgggcccct | actcccgcga | aaggccgaa | gccctcaagc | gggcggagct | tcccctcgag | 1080 |
| gccaagcggc | gccggggtta | tgccctggga | cgcctggacc | agctggcggt | ggagtacctc | 1140 |
| ctgggggtgc | gggggtga | | | | | 1158 |

<210> SEQ ID NO 10
<211> LENGTH: 385
<212> TYPE: PRT
<213> ORGANISM: Thermus thermophilus

<400> SEQUENCE: 10

Met Pro Lys Pro Glu His Arg Phe Thr Phe Gly Leu Trp Thr Val Gly
1               5                   10                  15

Asn Val Gly Arg Asp Pro Phe Gly Asp Ala Val Arg Glu Arg Leu Asp
            20                  25                  30

Pro Val Tyr Val Val His Lys Leu Ala Glu Leu Gly Ala Tyr Gly Val
        35                  40                  45

Asn Leu His Asp Glu Asp Leu Ile Pro Arg Gly Thr Pro Pro Gln Glu
    50                  55                  60

Arg Asp Gln Ile Val Arg Arg Phe Lys Lys Ala Leu Asp Glu Thr Gly
65                  70                  75                  80

Leu Lys Val Pro Met Val Thr Ala Asn Leu Phe Ser Asp Pro Ala Phe
                85                  90                  95

Lys Asp Gly Ala Phe Thr Ser Pro Asp Pro Trp Val Arg Ala Tyr Ala

```
                 100                 105                 110
Leu Arg Lys Ser Leu Glu Thr Met Asp Leu Gly Ala Glu Leu Gly Ala
        115                 120                 125
Glu Ile Tyr Val Val Trp Pro Gly Arg Glu Gly Ala Glu Val Glu Ala
    130                 135                 140
Thr Gly Lys Ala Arg Lys Val Trp Asp Trp Val Arg Glu Ala Leu Asn
145                 150                 155                 160
Phe Met Ala Ala Tyr Ala Glu Asp Gln Gly Tyr Gly Tyr Arg Phe Ala
                165                 170                 175
Leu Glu Pro Lys Pro Asn Glu Pro Arg Gly Asp Ile Tyr Phe Ala Thr
            180                 185                 190
Val Gly Ser Met Leu Ala Phe Ile His Thr Leu Asp Arg Pro Glu Arg
        195                 200                 205
Phe Gly Leu Asn Pro Glu Phe Ala His Glu Thr Met Ala Gly Leu Asn
    210                 215                 220
Phe Val His Ala Val Ala Gln Ala Leu Asp Ala Gly Lys Leu Phe His
225                 230                 235                 240
Ile Asp Leu Asn Asp Gln Arg Met Ser Arg Phe Asp Gln Asp Leu Arg
                245                 250                 255
Phe Gly Ser Glu Asn Leu Lys Ala Ala Phe Phe Leu Val Asp Leu Leu
            260                 265                 270
Glu Ser Ser Gly Tyr Gln Gly Pro Arg His Phe Asp Ala His Ala Leu
        275                 280                 285
Arg Thr Glu Asp Glu Glu Gly Val Trp Ala Phe Ala Arg Gly Cys Met
    290                 295                 300
Arg Thr Tyr Leu Ile Leu Lys Glu Arg Ala Glu Ala Phe Arg Glu Asp
305                 310                 315                 320
Pro Glu Val Lys Glu Leu Leu Ala Ala Tyr Tyr Gln Glu Asp Pro Ala
                325                 330                 335
Ala Leu Ala Leu Leu Gly Pro Tyr Ser Arg Glu Lys Ala Glu Ala Leu
            340                 345                 350
Lys Arg Ala Glu Leu Pro Leu Glu Ala Lys Arg Arg Arg Gly Tyr Ala
        355                 360                 365
Leu Gly Arg Leu Asp Gln Leu Ala Val Glu Tyr Leu Leu Gly Val Arg
    370                 375                 380
Gly
385

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      PRIMER FOR THERMUS THERMOPHILUS XYLA GENE.

<400> SEQUENCE: 11
tgatcaatgt acgagcccaa acc                                           23

<210> SEQ ID NO 12
<211> LENGTH: 16
<212> TYPE: DNA
```

-continued

```
<213> ORGANISM: Artificial Sequence
<220> FEATURE:
<223> OTHER INFORMATION: Description of Artificial Sequence:  SYNTHETIC
      PRIMER FOR THERMUS THERMOPHILUS XYLA GENE.

<400> SEQUENCE: 12
tgatcacccc cgcacc                                                    16
```